United States Patent
Wang et al.

(10) Patent No.: US 9,528,966 B2
(45) Date of Patent: Dec. 27, 2016

(54) REFLECTION-MODE PHOTOACOUSTIC TOMOGRAPHY USING A FLEXIBLY-SUPPORTED CANTILEVER BEAM

(75) Inventors: Lihong Wang, Creve Coeur, MO (US); Konstantin Maslov, Affton, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 13/125,522

(22) PCT Filed: Oct. 21, 2009

(86) PCT No.: PCT/US2009/061435
§ 371 (c)(1),
(2), (4) Date: Apr. 21, 2011

(87) PCT Pub. No.: WO2010/048258
PCT Pub. Date: Apr. 29, 2010

(65) Prior Publication Data
US 2011/0201914 A1    Aug. 18, 2011

Related U.S. Application Data

(60) Provisional application No. 61/107,845, filed on Oct. 23, 2008.

(51) Int. Cl.
*G01N 29/24*   (2006.01)
*A61B 5/00*    (2006.01)
(Continued)

(52) U.S. Cl.
CPC ......... *G01N 29/2418* (2013.01); *A61B 5/0059* (2013.01); *A61B 5/0095* (2013.01);
(Continued)

(58) Field of Classification Search
CPC ................ A61B 5/05; A61B 8/12; A61B 8/00
(Continued)

(56) References Cited

U.S. PATENT DOCUMENTS

| 4,255,971 A | 3/1981 | Rosencwaig |
| 4,267,732 A | 5/1981 | Quate |

(Continued)

FOREIGN PATENT DOCUMENTS

WO    2008/062354 A1    5/2008

OTHER PUBLICATIONS

Kolkman, R. G. M., et al, In Vivo Photoacoustic Imaging of Blood Vessels Using an Extreme-Narrow Aperture Sensor, Journal on Selected Topics in Quantum Electronics, pp. 343-346, vol. 9, 2003, IEEE.

(Continued)

*Primary Examiner* — Rochelle Turchen
(74) *Attorney, Agent, or Firm* — Armstrong Teasdale LLP

(57) ABSTRACT

Noninvasively imaging biological tissue using a handheld device. A light pulse is focused into a predetermined area inside an object using a flexibly mounted cantilever beam, acoustic waves emitted by the object in response to the at least one light pulse are detected by a transducer, and an image of the predetermined area inside the object is generated based on a signal generated by the transducer representative of the acoustic waves.

20 Claims, 13 Drawing Sheets

(51) Int. Cl.
*A61B 5/1455* (2006.01)
*A61B 8/00* (2006.01)
*A61B 8/06* (2006.01)
*G01N 29/06* (2006.01)

(52) U.S. Cl.
CPC .......... *A61B 5/14552* (2013.01); *A61B 5/415* (2013.01); *A61B 5/418* (2013.01); *A61B 5/4866* (2013.01); *A61B 8/00* (2013.01); *A61B 8/06* (2013.01); *A61B 8/4444* (2013.01); *G01N 29/0672* (2013.01); *G01N 2291/02475* (2013.01); *G01N 2291/0427* (2013.01)

(58) Field of Classification Search
USPC .......................................... 600/407, 473–476
See application file for complete search history.

(56) References Cited

U.S. PATENT DOCUMENTS

| | | | |
|---|---|---|---|
| 4,385,634 A | 5/1983 | Bowen | |
| 4,462,255 A | 7/1984 | Guess et al. | |
| 4,468,136 A | 8/1984 | Murphy et al. | |
| 4,546,771 A | 10/1985 | Eggleton et al. | |
| 5,373,845 A * | 12/1994 | Gardineer et al. | 600/445 |
| 5,465,722 A | 11/1995 | Fort et al. | |
| 5,713,356 A | 2/1998 | Kruger | |
| 5,718,231 A * | 2/1998 | Dewhurst et al. | 600/462 |
| 5,840,023 A * | 11/1998 | Oraevsky et al. | 600/407 |
| 6,216,025 B1 | 4/2001 | Kruger | |
| 6,498,942 B1 | 12/2002 | Esenaliev et al. | |
| 6,545,264 B1 | 4/2003 | Stern | |
| 6,567,688 B1 | 5/2003 | Wang | |
| 6,626,834 B2 * | 9/2003 | Dunne et al. | 600/444 |
| 6,633,774 B2 | 10/2003 | Kruger | |
| 6,694,173 B1 | 2/2004 | Bende et al. | |
| 6,764,450 B2 | 7/2004 | Yock | |
| 6,833,540 B2 | 12/2004 | MacKenzie et al. | |
| 6,839,496 B1 | 1/2005 | Mills et al. | |
| 6,846,288 B2 | 1/2005 | Nagar et al. | |
| 6,877,894 B2 | 4/2005 | Vona et al. | |
| 6,937,886 B2 | 8/2005 | Zavislan | |
| 7,198,778 B2 | 4/2007 | Achilefu et al. | |
| 7,266,407 B2 | 9/2007 | Li et al. | |
| 7,357,029 B2 | 4/2008 | Falk | |
| 2002/0093637 A1 | 7/2002 | Yuan | |
| 2004/0039379 A1 | 2/2004 | Viator et al. | |
| 2004/0082070 A1 * | 4/2004 | Jones et al. | 436/8 |
| 2004/0254474 A1 * | 12/2004 | Seibel et al. | 600/473 |
| 2005/0015002 A1 * | 1/2005 | Dixon et al. | 600/407 |
| 2005/0154313 A1 * | 7/2005 | Desilets et al. | 600/459 |
| 2005/0234315 A1 | 10/2005 | Mayevsky | |
| 2006/0122516 A1 * | 6/2006 | Schmidt et al. | 600/476 |
| 2006/0184042 A1 | 8/2006 | Wang et al. | |
| 2006/0235299 A1 | 10/2006 | Martinelli | |
| 2007/0088206 A1 | 4/2007 | Peyman et al. | |
| 2007/0213590 A1 | 9/2007 | Squicciarini | |
| 2007/0213618 A1 * | 9/2007 | Li et al. | 600/476 |
| 2007/0213693 A1 | 9/2007 | Plunkett | |
| 2008/0029711 A1 | 2/2008 | Viellerobe | |
| 2008/0173093 A1 | 7/2008 | Wang et al. | |
| 2009/0088631 A1 * | 4/2009 | Dietz et al. | 600/424 |
| 2009/0116518 A1 | 5/2009 | Patel et al. | |
| 2010/0268042 A1 | 10/2010 | Wang | |

OTHER PUBLICATIONS

Maslov, K., et al, In Vivo Dark-Field Reflection-Mode Photoacoustic Microscopy, Optics Letters 30, pp. 625-627, 2005.

Savateeva, E., et al., Noninvasive Detection and Staging of Oral Cancer in Vivo with Confocal Opto-Acoustic Tomography, Proceedings of SPIE, pp. 55-66, vol. 3916, 2000.

Zhang, H.F., et al., In Vivo Imaging of Subcutaneous Structures Using Functional Photoacoustic Microscopy, Nature Protocols, pp. 797-804, vol. 2, 2007.

Holelen, G. A., et al, Three-Dimensional Photoacoustic Imaging of Blood Vessels in Tissue, Optics Lefferts, pp. 648-650, vol. 23, No. 8, 1998, Optical Society of America.

Foster, Stuart F., et al, Advances in Ultrasound Biomicroscopy, Ultrasound in Med. & Biol, pp. 1-27, vol. 26, No. 1, 2000, World Federation for Ultrasound in Medicine & Biology, Elsevier.

Zhang, H. F., et al., Functional Photoacoustic Microscopy for High-Resolution and Noninvasive in Vivo Imaging, Nature Biotechnology Letters, pp. 848-851, vol. 24, No. 7, 2006, Nature Publishing Group.

PCT, Notification of Transmittal of the International Search Report and the Written Opinion of the International Searching Authority, or the Declaration, for PCT/US2009/061435, dated Mar. 29, 2010, 10 pages.

Final Office Action from related U.S. Appl. No. 13/450,793 dated Nov. 22, 2013; 22 pgs.

Non-Final Office Action from related U.S. Appl. No. 13/450,793 dated Mar. 24, 2014; 22 pgs.

Non-Final Office Action from related U.S. Appl. No. 13/143,832 dated Apr. 18, 2014, 14 pgs.

* cited by examiner

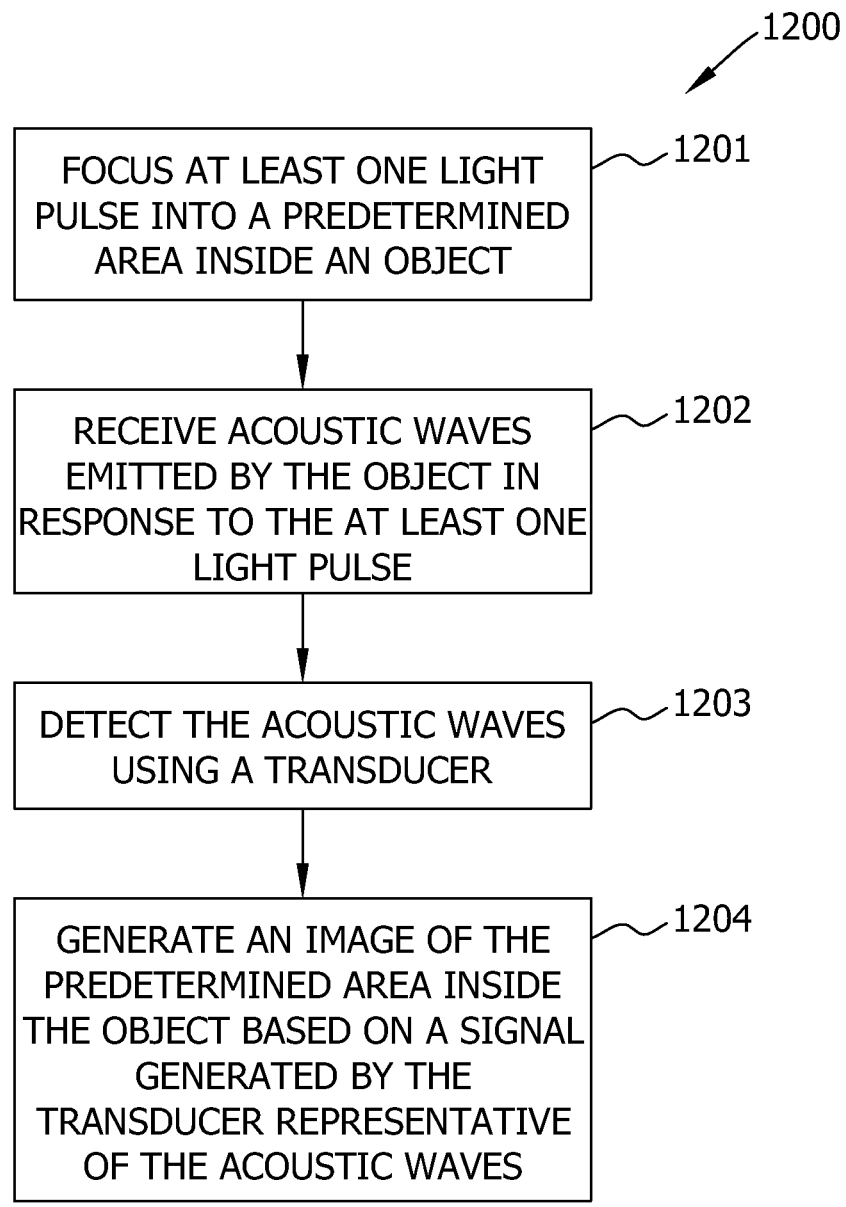

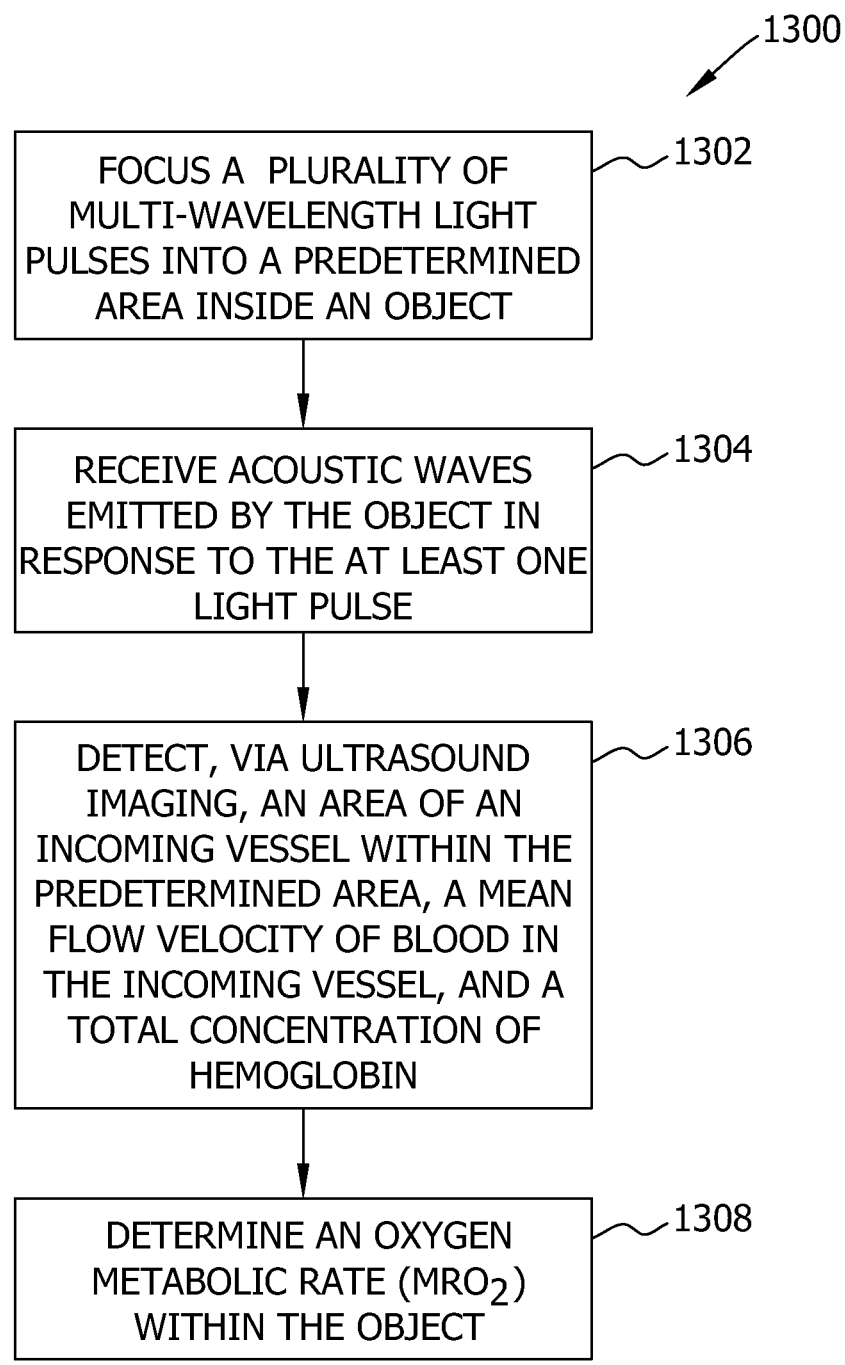

REFLECTION-MODE PHOTOACOUSTIC TOMOGRAPHY USING A FLEXIBLY-SUPPORTED CANTILEVER BEAM

CROSS-REFERENCE TO RELATED APPLICATIONS

This application is a 35 U.S.C. §371 national stage application of PCT/US2009/061435, filed Oct. 21, 2009, which claims priority to U.S. Provisional Application No. 61/107,845, Oct. 23, 2008, the entireties of which are hereby incorporated by reference for all purposes.

STATEMENT REGARDING FEDERALLY SPONSORED RESEARCH & DEVELOPMENT

This invention was made with government support under grant R01 NS046214 awarded by the U.S. National Institutes of Health. The government has certain rights in the invention.

BACKGROUND

The subject matter disclosed herein relates generally to photoacoustic imaging and, more specifically, to using photoacoustic tomography to characterize a target or targeted area within a tissue.

At least some known photoacoustic imaging systems provide high-quality images using a hand-held scanning probe. From an instrumentation point of view, photoacoustic imaging relies heavily on ultrasound detection technology. As such at least some known photoacoustic imaging systems have largely focused on customized ultrasound transducers or scanning systems. However, such photoacoustic imaging systems do not include real-time mechanical scanning capabilities.

For example, at least one known ultrasound-based high-resolution in vivo micro-imaging system uses a single-element scanning ultrasonic imaging platform. Such a system has the ability to visualize in real time and quantify animal anatomical targets, hemodynamics (blood flow), and therapeutic interventions with resolution down to approximately 30 microns. Moreover, such a system includes a power Doppler capability to visualize and quantify relative blood flow in vivo for anti-angiogenic studies. Using such a system enables acquisition of at least 100 frames per second (fps). Further, such a system may be used for high-resolution imaging within a depth of ~20 mm which diffuse light can still penetrate.

However, while ultrasonic imaging is primarily based on acoustic impedance inhomogeneity, photoacoustic imaging is based on optical absorption contrast, which is as strong as 5000% between blood or melanin and the surrounding tissue at some optical wavelengths and contains information about tissue molecular composition or physiological status (e.g., blood oxygenation). Therefore, optical and ultrasonic contrasts are complementary and optical contrasts can open new possibilities for in vivo imaging. For example, the combination of the above-described system's ability to measure blood velocity and photoacoustic imaging's ability to measure blood oxygenation as well as blood hemoglobin concentration makes possible real-time measurements of tissue metabolic rate. Moreover, photoacoustic imaging may help such an ultrasonic imaging system identify certain light absorbing structures such as blood vessels or melanin-rich melanomas and to use optical absorption based contrast agents such as nanostructures or FDA approved indocyanine green (ICG) dye for molecular imaging. With the help of dye, photocacoustic imaging may also be used to identify sentinel lymph nodes.

Accordingly, a method and apparatus is desirable that combines ultrasound-based high-resolution in vivo micro-imaging systems, such as those described above, with photoacoustic imaging using a flexibly mounted cantilever beam.

SUMMARY

In one aspect, a method is provided for noninvasively imaging biological tissue using a handheld device. The method includes focusing at least one light pulse into a predetermined area inside an object using a flexure mounted cantilever beam, receiving acoustic waves emitted by the object in response to the at least one light pulse, detecting the acoustic waves using a transducer, and generating an image of the predetermined area inside the object based on a signal generated by the transducer representative of the acoustic waves.

In another aspect, a method is provided for determining an oxygen metabolic rate ($MRO_2$) within a biological tissue using a handheld device. The method includes focusing a plurality of multi-wavelength light pulses into a predetermined area inside an object, and receiving acoustic waves emitted by the object in response to the at least one light pulse. The method also includes determining the $MRO_2$ based on an area of an incoming vessel within the predetermined area, a mean flow velocity of blood in the incoming vessel, and a total concentration of hemoglobin, wherein the area of the incoming vessel and the mean flow velocity may are based on measurements obtained by ultrasound imaging, and wherein the total concentration of hemoglobin is based on measurements obtained by the plurality of multi-wavelength light pulses.

In another aspect, a handheld device is provided for use in noninvasive imaging of biological tissue using photoacoustic tomography. The device includes a laser, an optical assembly configured to focus at least one light pulse emitted by the laser into a predetermined area inside an object, and a transducer configured to detect acoustic waves emitted by the object in response to the at least one light pulse. The optical assembly and the transducer are positioned on a cantilever beam that is flexibly mounted within a closed, liquid-filled container to facilitate one-dimensional or two-dimensional scanning of the predetermined area inside the object.

BRIEF DESCRIPTION OF THE DRAWINGS

The embodiments described herein may be better understood by referring to the following description in conjunction with the accompanying drawings.

FIG. 12 is a flowchart illustrating an exemplary photoacoustic tomography imaging method.

FIG. 13 is a flowchart illustrating an exemplary method for determining an oxygen metabolic rate within a biological tissue.

DETAILED DESCRIPTION

Figure 1:
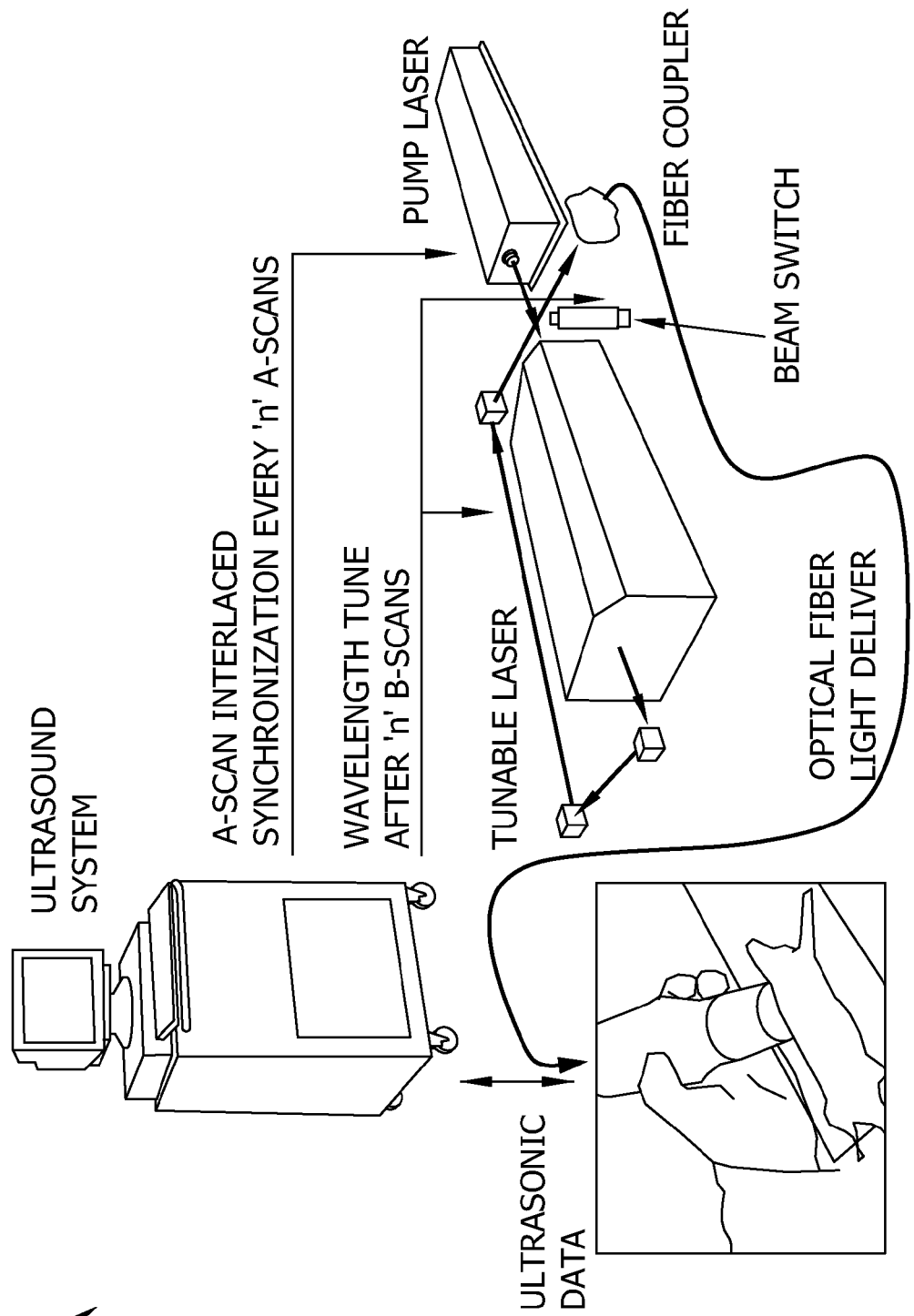
FIG. 1 is a block diagram of an imaging system that includes an ultrasonic imaging system and a photoacoustic scanner.

While the making and using of various embodiments of the invention are discussed in detail below, it should be appreciated that the embodiments of the invention provides many applicable inventive concepts that may be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the embodiments of the invention. Terms such as "a," "an" and "the" are not intended to refer to only a singular entity, but include the general class of which a specific example may be used for illustration. The terminology herein is used to describe specific embodiments of the invention, but their usage does not delimit the invention, except as outlined in the claims.

To be consistent with the commonly used terminology, whenever possible, the terms used herein will follow the definitions recommended by the Optical Society of America (OCIS codes).

In some embodiments, term "photoacoustic microscopy" refers to a photoacoustic imaging technology that detects pressure waves generated by light absorption in the volume of a material (such as biological tissue) and propagated to the surface of the material. In other words, photoacoustic microscopy is a method for obtaining images of the optical contrast of a material by detecting acoustic or pressure waves traveling from the object. The emphasis is on the micrometer scale image resolution.

In some embodiments, the term "photoacoustic tomography" also refers to a photoacoustic imaging technology that detects acoustic or pressure waves generated by light absorption in the volume of a material (such as biological tissue) and propagated to the surface of the material. The emphasis is sometimes on computer-based image reconstruction although photoacoustic tomography encompasses photoacoustic microscopy.

In some embodiments, the term "piezoelectric detectors" refers to detectors of acoustic waves utilizing the principle of electric charge generation upon a change of volume within crystals subjected to a pressure wave.

In some embodiments, the terms "reflection mode" and "transmission mode" refer to a laser photoacoustic microscopy system that employs the detection of acoustic or pressure waves transmitted from the volume of their generation to the optically irradiated surface and a surface that is opposite to, or substantially different from, the irradiated surface, respectively.

In some embodiments, the term "time-resolved detection" refers to the recording of the time history of a pressure wave with a temporal resolution sufficient to reconstruct the pressure wave profile.

In some embodiments, the term "transducer array" refers to an array of ultrasonic transducers.

In some embodiments, the terms "focused ultrasonic detector," "focused ultrasonic transducer," and "focused piezoelectric transducer" refer to a curved ultrasonic transducer with a hemispherical surface or a planar ultrasonic transducer with an acoustic lens attached or an electronically focused ultrasonic array transducer.

In some embodiments, the terms "transducer array" and "phase array transducer" refer to an array of piezoelectric ultrasonic transducers.

In some embodiments, the term "photoacoustic waves" refers to pressure waves produced by light absorption.

As will be described below, embodiments of the invention provide a method of characterizing a target within a tissue by focusing one or more laser pulses on the region of interest in the tissue so as to penetrate the tissue and illuminate the region of interest. The pressure waves induced in the object by optical absorption are received using one or more ultrasonic transducers that are focused on the same region of interest. The received acoustic waves are used to image the structure or composition of the object. The one or more laser pulses are focused by an optical assembly, typically including optical fibers, lenses, prisms and/or mirrors, which converges the laser light towards the focal point of the ultrasonic transducer. The focused laser light selectively heats the region of interest, causing the object to expand and produce a pressure wave whose temporal profile reflects the optical absorption and thermo-mechanical properties of the object. In addition to a single-element focused ultrasonic transducer, an annular array of ultrasonic transducers may be used to enhance the depth of field of the imaging system by using synthetic aperture image reconstruction. The assembly of the ultrasonic transducer and laser pulse focusing optics are positioned on a cantilever beam and scanned together, performing fast one- or two-directional sector scanning of the object. The cantilever beam is suspended inside a closed, liquid filled container, which has an acoustically and optically transparent window on a side of the transducer-light delivery optics assembly. The window may be permanent or disposable. The window is positioned on an object surface, where acoustic coupling gel is applied. Neither immersion of the object in water nor movement of the scanner relative to the object surface is necessary to perform imaging.

Further, a linear transducer array, focused or unfocused in elevation direction, may be used to accelerate image formation. The signal recording includes digitizing the received acoustic waves and transferring the digitized acoustic waves to a computer for analysis. The image of the object is formed from the recorded acoustic waves.

In addition, embodiments of the invention may also include one or more ultrasonic transducers or a combination thereof. The electronic system includes scanner drivers and controllers, an amplifier, a digitizer, laser wavelength tuning electronics, a computer, a processor, a display, a storage device or a combination thereof. One or more components of the electronic system may be in communication remotely with the other components of the electronic system, the scanning apparatus or both.

The imaging method described herein, which uses a confocal photoacoustic imaging system, is one of the possible embodiments, specifically aimed at medical and biological applications but not limited to these applications. The embodiments of the invention are complementary to pure optical and ultrasonic imaging technologies and may be used for diagnostic, monitoring or research purposes. The main applications of the technology include, but are not limited to, the imaging of arteries, veins, capillaries (the smallest blood vessels), pigmented tumors such as melanomas, hematomas, acute burns, and or sentinel lymphatic nodes in vivo in humans or animals. Embodiments of the invention may use the spectral properties of intrinsic optical contrast to monitor blood oxygenation (oxygen saturation of hemoglobin), blood volume (total hemoglobin concentration), and even the metabolic rate of oxygen consumption; it may also use the spectral properties of a variety of dyes or other contrast agents to obtain additional functional or molecular-specific information. In other words, embodiments of the invention are capable of functional and molecular imaging.

Finally, embodiments of the invention may be used to monitor possible tissue changes during x-ray radiation therapy, chemotherapy, or other treatment, and may also be used to monitor topical application of cosmetics, skin creams, sun-blocks or other skin treatment products. Embodiments of the invention, when miniaturized, may also be used endoscopically. e.g., for the imaging of atherosclerotic lesions in blood vessels or precancerous and cancerous lesion in the gastrointestinal tract.

To incorporate photoacoustic imaging into an ultrasonic scanning system or imaging system 100, a photoacoustic excitation source, such as a tunable pulsed dye laser, and a light delivery system are introduced to the ultrasonic scanning system 100 as shown in FIG. 1. The light delivery system, including an optical fiber and light focusing optics, are integrated into the handheld ultrasonic scanner. Light from either the pump laser (before frequency doubling) or the tunable dye laser may be selected with a beam switch and coupled into the optical fiber. The laser must be synchronized with the imaging system 100. In the exemplary embodiment, the imaging system 100 interlaces trigger pulses between the laser and the ultrasonic pulser. The imaging system 100 also controls the emission wavelength of the tunable laser. The light focusing optics is placed inside the ultrasonic scanning head.

Figure 2:
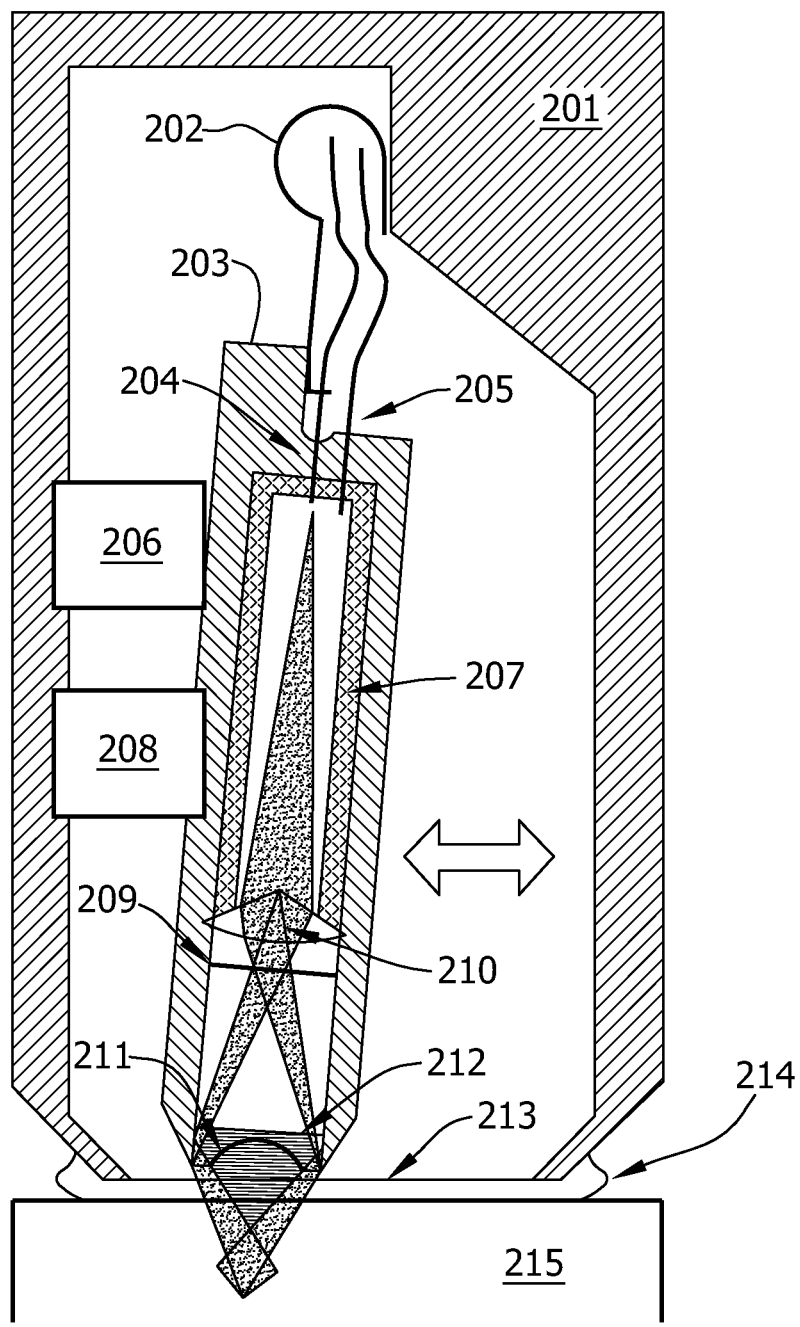
FIG. 2 is a schematic diagram of an exemplary direct contact dark-field photoacoustic microscopy scanner.

FIG. 2 is a diagram of an exemplary photoacoustic scanner 200 of the imaging system in accordance with one embodiment of the invention. As shown in FIG. 2, scanner 200 is implemented as a handheld device. A dye laser, pumped by a Q-switched pulsed neodymium-doped yttrium lithium fluoride (Nd:YLF) laser delivers approximately 1.0 millijoules (mJ) per pulse to a 0.60-mm diameter optical fiber 204. The laser pulse width is approximately 8.0 nanoseconds (ns), and the pulse repetition rate varies from approximately 0.1 kilohertz (kHz) to approximately 2.0 kHz. The fiber output 204 is coaxially positioned with a focused ultrasonic transducer 211. The concave bowl-shaped transducer 211 has a center frequency of approximately 30.0 megahertz (MHz) and a nominal bandwidth of 100%. The laser light from the fiber 204 is expanded by a conical lens 210 and then focused through an annular hollow cone shaped optical condenser 212, which also serves as a back-plate of the ultrasonic transducer. The optical focal region overlaps with the focal spot of the ultrasonic transducer 211, thus forming a confocal optical dark-field illumination and ultrasonic detection configuration. The photoacoustic setup is mounted inside a hollow cylindrical cantilever beam 203 supported by a flexure bearing 202. The cantilever beam 203 is mounted inside a container 201. The container is filled with immersion liquid and sealed with an optically and acoustically transparent membrane 213. The object 215, e.g., animal or human, is placed outside the container 201 below the membrane 213, and the ultrasonic coupling is further secured by coupling gel 214. The cantilever beam is moved by an actuator 206, and its inclination angle is controlled by a sensor 208. Part of the laser pulse energy is reflected from the focusing optics, such as a conical lens 210, and after multiple reflections from the diffusely reflecting coating of the integrating chamber 207, is detected by a photodetector 205. The signal from the photo-detector 205 is used as a reference signal to take into account energy fluctuations of the laser output. An aperture diaphragm 209 screens the photo-detector 205 from ambient light and sample surface reflection.

Compared to alternative designs, the above design provides the following advantages. First, the high axial stiffness of the cantilever beam increases repeatability of the axial position of the photoacoustic detector. Second, the frictionless flexure bearing pivot decreases the lateral position error of the photoacoustic detector and the mass of the system, thereby decreasing mechanical vibration (noise) of the scanner and increasing its overall mechanical stability. Third, the sealed container design makes the photoacoustic scanner portable and ergonomic, which widens the application field of the photoacoustic technique, especially in medical and biological practice. Fourth, the device performs interlaced acquisition of time-resolved laser-induced pressure waves and reflected ultrasonic pulses, which may be used, for example, to measure the tissue metabolic rate through co-registration of ultrasound pulsed-Doppler and photoacoustic spectral data at high temporal and spatial resolution.

Figure 3:
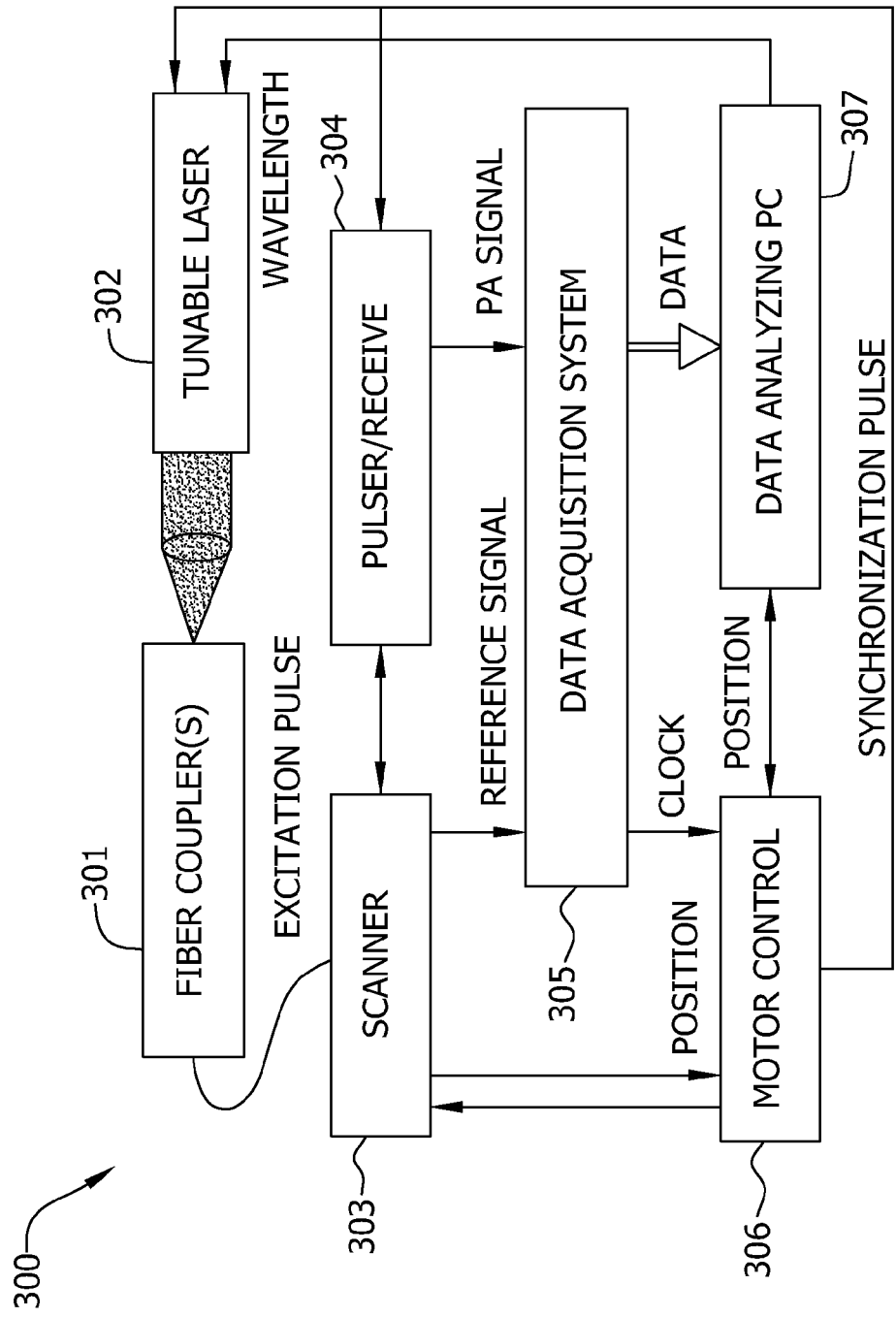
FIG. 3 is a block diagram of an exemplary quantitative spectroscopic measurement system that includes the photoacoustic microscopy scanner shown in FIGS. 1 and 2.

FIG. 3 is a block diagram of an exemplary photoacoustic system 300 that uses dark-field photoacoustic microscopy with sector scanning and quantitative spectroscopic measurement capability in accordance with one embodiment of the invention. The system includes a light delivery subsystem that includes of a tunable pulsed laser subsystem 302, an optical fiber or fibers and the associated fiber coupling optics 301, a scanner 303 that includes a light focusing device and one or more ultrasonic transducers, and an electronic system that may include an ultrasonic pulser/receiver 304, a motion controller 306, a data acquisition system 305, and a data-analyzing computer 307. Depending on the particular application, the photoacoustic system 300 may have an array of peripheral devices (not shown) such as manipulation arm, health and environment monitoring devices, and data storage. The focusing device of the scanner 303 is connected to an output of the fiber coupler 301 via single or multiple optical fibers that receive one or more laser pulses from the tunable laser 302 and focus the one or more laser pulses into a tissue so as to illuminate the tissue. The one or more ultrasonic transducers positioned alongside the focusing optics are focused on the region of interest and receive acoustic or pressure waves induced in the object by the laser light. The electronic system records and processes the received acoustic or pressure waves and controls scanner motion. Ultrasonic transducers may work in two modes, as a receiving transducer for photoacoustic signals and as a pulser/receiver for conventional pulse/echo ultrasonic imaging. The focusing device includes an optical assembly of lenses, prisms, and/or mirrors that expands and subsequently converges the laser light toward the focal point of the one or more ultrasonic transducers.

The dark field confocal photoacoustic sensor is placed on a cantilever beam to perform sector scanning along the tissue surface. The near-simultaneously (e.g., approximately 20.0 microsecond (μs) delayed) recorded photoacoustic and pulse/echo pressure-wave time histories are displayed by the data-analyzing PC 307 versus the photoacoustic sensor position to construct co-registered images of the distribution of the optical and mechanical contrast within the tissue. Depending on the type of scanning (e.g., one or two axis), the device produces cross-sectional (B-scan) or volumetric images of the tissue structure. When the tissue under investigation is an internal organ, the optical fiber and transducer may be incorporated in an endoscope and positioned inside the body.

The data acquisition subsystem 305 produces a clock signal to synchronize all electronic components of the photoacoustic device. The motor controller 306 drives the cantilever beam actuators and measures the current position of the photoacoustic transducer. At transducer locations predefined by the data-analyzing computer 307, the motor controller generates trigger pulses synchronized with the clock signal, which are used to trigger the pulse laser and start the data acquisition sequence.

High-frequency ultrasonic waves generated in the tissue by the laser pulse are recorded and analyzed by the data analyzing computer 307 to reconstruct an image. The shape and dimensions of the optical-contrast tissue structures are generally determined from the temporal profile of the laser-induced ultrasonic waves and the position of the focused ultrasonic transducer. A single axis sector scanning by the ultrasonic transducer positioned within the cantilever beam is used to form a two-dimensional image, and two-axis scanning is used to form a three-dimensional image. However, a transducer array may be used to reduce the time of scanning and light exposure. The following examples are provided for the purpose of illustrating various embodiments of the invention, and are not meant to limit the embodiments of the invention in any fashion.

To obtain functional images, laser pulses from a tunable laser (e.g., a dye laser) are used to illuminate the tissue surface. By switching between several light wavelengths, the optical absorption spectrum of a tissue structure may be measured. This spectrum is influenced by the dispersion of optical absorption and scattering in the object. Nevertheless, in cases where the tissue absorption has definite and distinct spectral features, which is the case, for example, with oxyhemoglobin and deoxyhemoglobin, by using a proper minimization procedure it is possible to separate the contributions of different tissue constituents, and thus permit the measurement of local blood oxygenation in the tissue in order to separate normal and diseased tissues. Similarly, certain tumors may be identified by targeting them with biomolecules conjugated to various contrast agents such as selectively absorbing dyes.

Embodiments of the invention may include any realization of a photoacoustic imaging device which uses a cantilever beam to perform object scanning. The following devices may implement the method described herein: a semi-rigid cantilever beam supported by a flexure bearing, a fixed end flexible cantilever beam, a cantilever beam with two degrees of freedom supported by two perpendicular flexure bearings, and a cantilever beam supported by a flexure bearing attached to a linear scanning stage.

Figure 4:
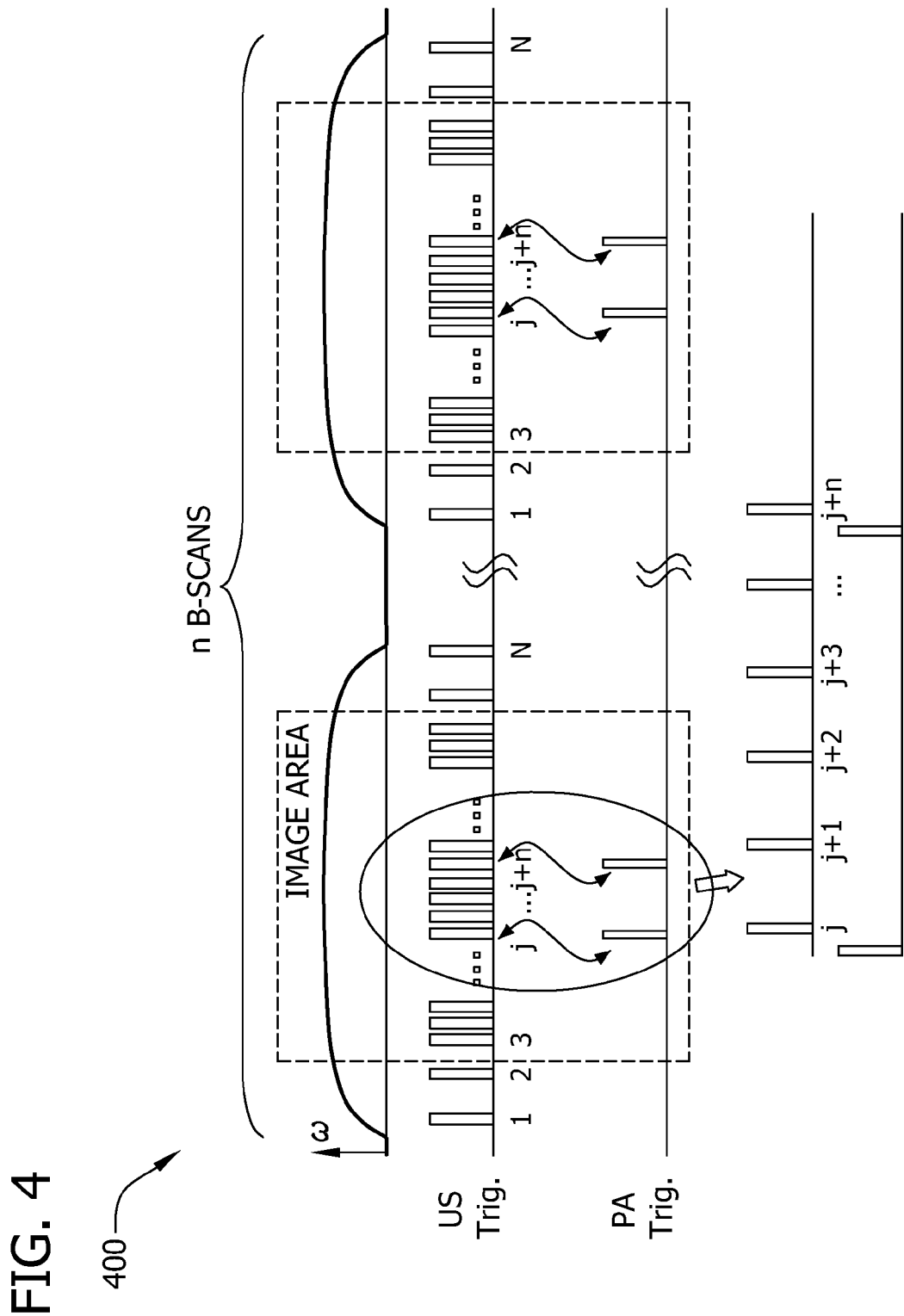
FIG. 4 is a timing diagram for photoacoustic imaging used by the scanner shown in FIGS. 1-3.

To synchronize the optical and ultrasonic components of the ultrasonic-based photoacoustic imaging system, the ultrasonic system shown in FIGS. 1-3 generates a triggering signal for the pulsed laser as shown in the timing diagram 400 of FIG. 4. The ultrasonic system acquires signals from the ultrasonic transducer and reference photo-detector and superimposes and/or codisplays photoacoustic images and ultrasound pulse-echo images. More specifically, a pump laser produces a pulse energy of approximately 20.0 mJ at a fundamental wavelength of approximately 1056.0 nm, and/or a tunable dye laser produces a pulse energy of greater than approximately 2.0 mJ at a frequency of up to approximately 2.0 kHz. The laser system thus provides approximately 8.0 ns wide laser pulses, which are short enough for the targeted spatial resolution. The ANSI safety limits are satisfied for a pulse energy less than or equal to approximately 2.0 mJ, a diameter of illumination greater than or equal to approximately 6.0 mm, a laser frequency less than or equal to approximately 2.0 kHz, and a scanning step size greater than or equal to approximately 0.1 mm. At 2 kHz PRF, the data acquisition time for a B-scan frame consisting of 200 A-lines is approximately 100.0 ms, yielding a B-scan frame rate of approximately 10.0 Hz. When approximately 20.0 mJ of pulse energy is used for deep penetration, the illumination area is increased to greater than or equal to approximately 1.0 cm$^2$ and the laser PRF decreased to approximately 50.0 Hz. Taking into account the decreased resolution for deep imaging, a B-scan frame rate of approximately 1.0 Hz is achieved if fifty A-lines are acquired to per B-scan.

Moreover, the ultrasonic scanning system generates one photoacoustic imaging synchronization signal for every n pulse-echo ultrasonic triggering pulses (shown as trigger pulses j and j+n in the timing diagram in FIG. 4), where n is approximately the ratio of the ultrasound PRF to the laser PRF. As the ultrasonic scanning progresses into the next frame (Bscan), the laser triggers will be generated in connection with pulse-echo triggers j+1 and j+n+1 correspondingly. After n consecutive frames of scanning, a complete photoacoustic image will be acquired, and the cycle will continue. At this time, the ultrasonic scanning system generates a control word to change the wavelength of the dye laser emission if spectral information is to be collected. Because the photoacoustic imaging system works at a fraction of the frame rate of the ultrasonic system, laser triggers will be simply introduced between consecutive pulse-echo triggers a few microseconds depending on imaging depth (e.g., approximately 20.0 μs is for a depth of approximately 30.0 mm) ahead of the corresponding pulse-echo trigger. This lead time will be sufficient for the data acquisition of photoacoustic data before the ultrasonic pulser applies a high voltage to the ultrasonic transducer. This mode of operation does not compromise the pure ultrasonic frame rate while the maximum photoacoustic imaging frame rate is achieved.

Various examples of photoacoustic scanners will now be described in reference to FIGS. 5-7, wherein the photoacoustic sensor includes an optical focusing device and one or more ultrasonic transducers.

The embodiments of the invention provides fast (e.g., approximately thirty frames per second) high resolution photoacoustic imaging of biological tissues in vivo. This particular embodiment has a lateral resolution as high as approximately 50.0 micrometers (μm) and an imaging depth limit of about 5.0 mm. The image resolution may be further improved by either increasing the frequency and bandwidth of the ultrasonic transducer or increasing the numerical aperture of the optical objective lens. The latter applies when imaging within the depth of one optical transport mean free path is desired. With the help of an ultrasonic array transducer, faster photoacoustic imaging is possible and signal averaging, when needed, is also realistic.

Embodiments of the invention may include any realization of light focusing any kind of mirrors, prisms, lenses, fibers, and diaphragms that may produce illumination directed to the focal area of the focused ultrasonic transducer if sector scanning of the object is performed. Embodiments of the invention may also include any photoacoustic techniques with any light delivery and ultrasonic detection arrangement placed inside a sealed container for scanning, where the container may remain motionless during acquisition of one image frame.

The following devices may be used to implement photoacoustic sensing for the purpose described herein: (1) a bowl-shaper focusing ultrasonic transducer; (2) a flat ultrasonic transducer attached to an acoustic lens; (3) a linear or (4) an annular focused or unfocused ultrasonic transducer array combined with an optical microscope annular condenser which may consist of lenses, mirrors, prisms or their combination. Various examples of the photoacoustic assembly suitable to be placed inside the hollow cantilever beam will now be described in reference to FIGS. 5-7 wherein the focusing assembly includes an optical focusing device and one or more ultrasonic transducers.

Figure 5:
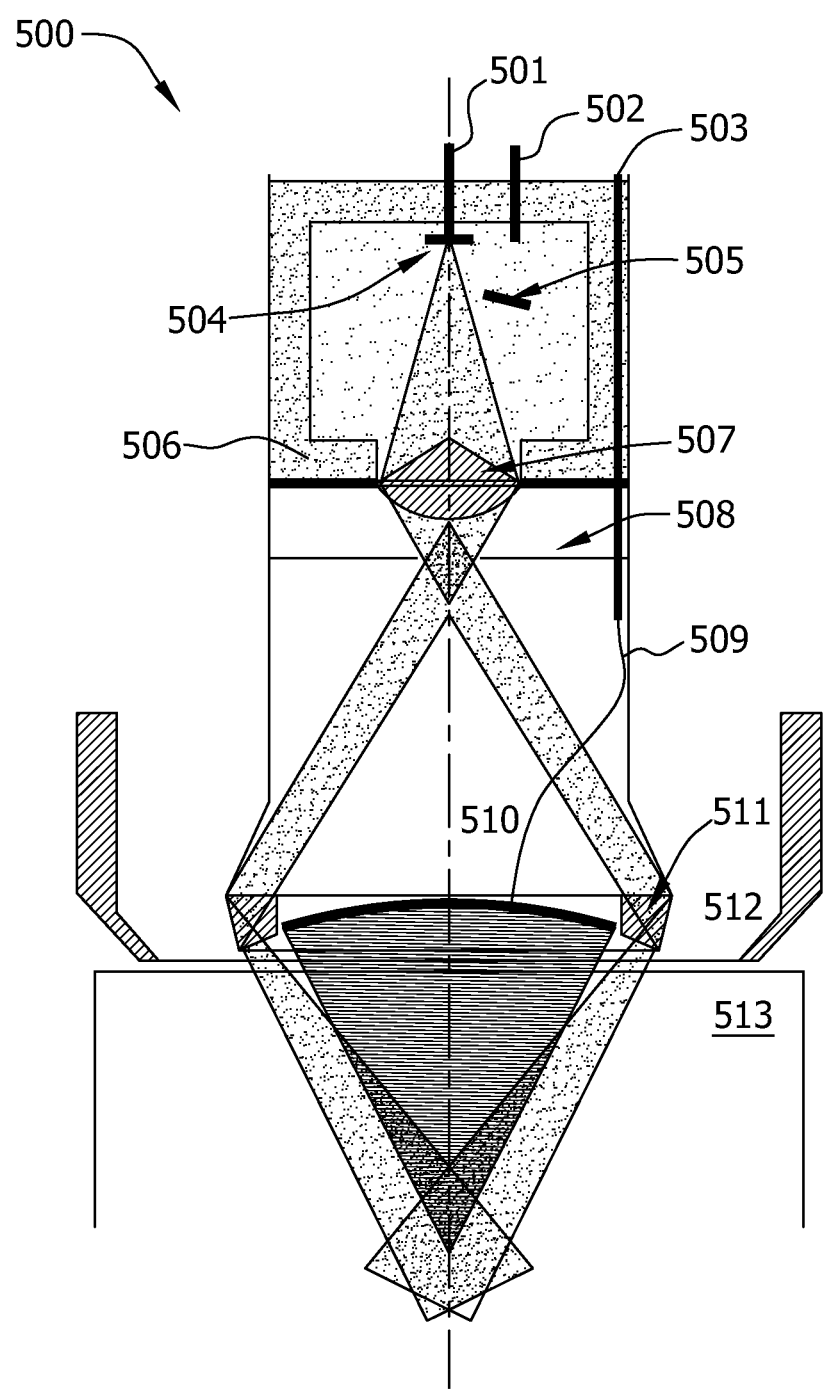
FIG. 5 is a schematic diagram of an exemplary photoacoustic head that may be used with the measurement system shown in FIG. 3, including a single-element spherically focusing transducer.

A diagram of a photoacoustic sensor assembly 500 of the imaging system in accordance with the main embodiment of the embodiments of the invention is shown in FIG. 5. More specifically, FIG. 5 shows a diagram of one embodiment of a photoacoustic sensor 500 in accordance with the scanner design shown in FIG. 1. A laser pulse is delivered via optical fiber 501, expanded by a conical lens 507, passed around the ultrasonic transducer 510, and focused by a conical prism 511. The transducer 510, focusing optics 507 and 511, optical fibers 501 and 502, and electrical wires connecting the transducer are placed inside the cylindrically shaped cantilever beam 509. In a non-scattering object, the laser energy distribution along the ultrasonic transducer axis would be confined to the transducer's depth of focus. In highly scattering media, the laser energy distribution is broader. The laser light penetrates through the transparent membrane 512 and the surface of the object 513 to a sufficient depth, selectively heating targets in the tissue that have higher optical absorption and producing ultrasonic waves. The ultrasonic waves that propagate toward the tissue surface are detected by an acoustic transducer 510, and digitized and transferred to a computer for data analysis. Part of the energy of the laser pulse is reflected from the lens surface, and the reflected light is homogenized by multiple reflections from the diffusively reflective coating of an integrating chamber 506 and reaches the sensing optical fiber 502. The output of the sensing optical fiber 502 is connected to a photo-detector (not shown). This measurement is used to compensate for the fluctuations in the laser output. An iris diaphragm 508 prevents most ambient light from entering the integrating chamber. An optical absorber 504 absorbs collimated back reflected and ambient light, which enters the integrating chamber through the iris aperture. A baffle 505 shields the sensing fiber from direct exposure to light reflected from the conical lens.

Figure 6:
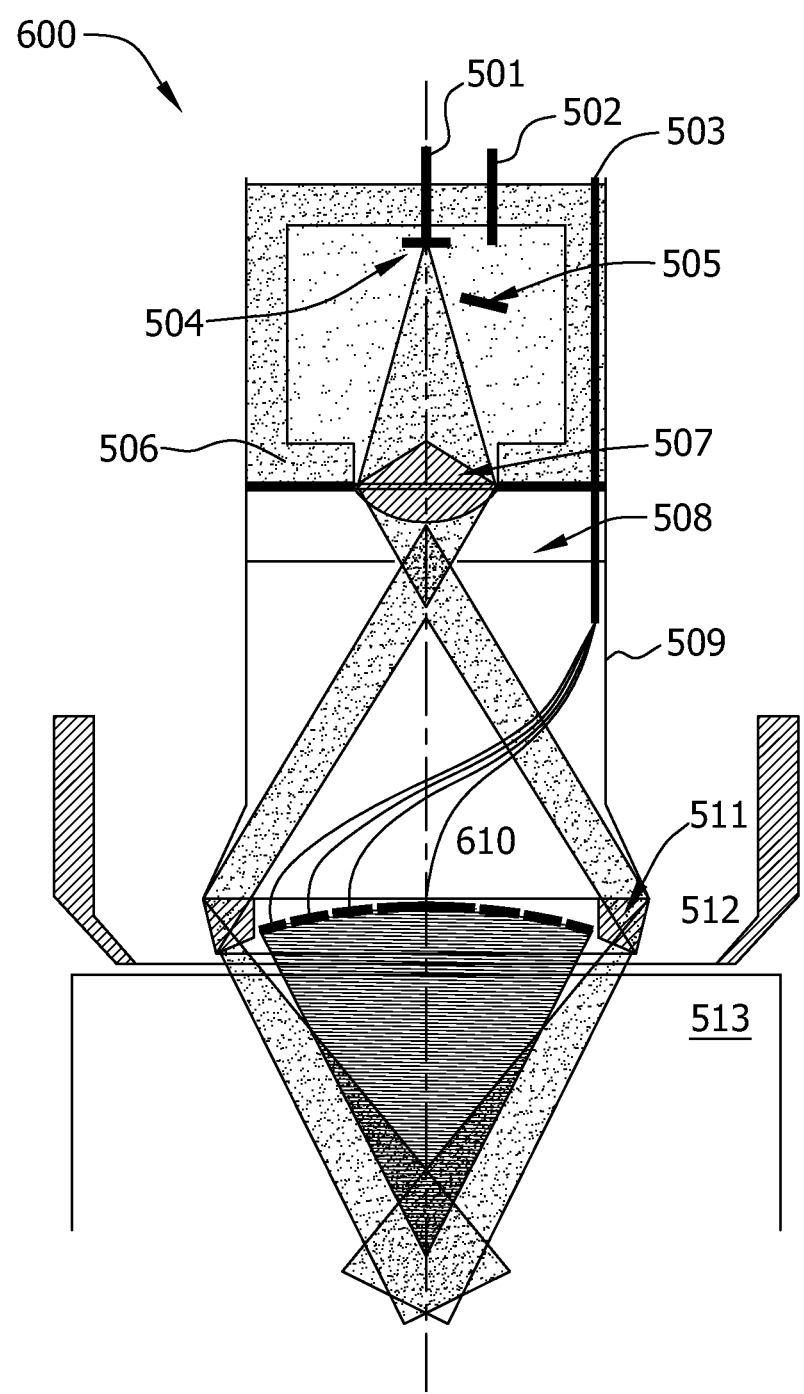
FIG. 6 is a schematic diagram of a second exemplary photoacoustic head that may be used with the measurement system shown in FIG. 3, including a spherically focusing annular transducer array.

FIG. 6 shows a diagram of another embodiment of a photoacoustic sensor 600 of the imaging system in accordance with FIG. 1. The photoacoustic sensor 600 is similar to photoacoustic sensor 500 (shown in FIG. 5), except that the single-element focused ultrasonic transducer is replaced with a multi-element annular piezoelectric transducer array 610. The ultrasonic transducer array 610 may be dynamically focused to different depths for a single laser pulse by introducing time-offlight-dependent time delays between signals from different transducer elements, thus extending the depth range of the cross-sectional (B-scan) image with high lateral resolution.

Figure 7:
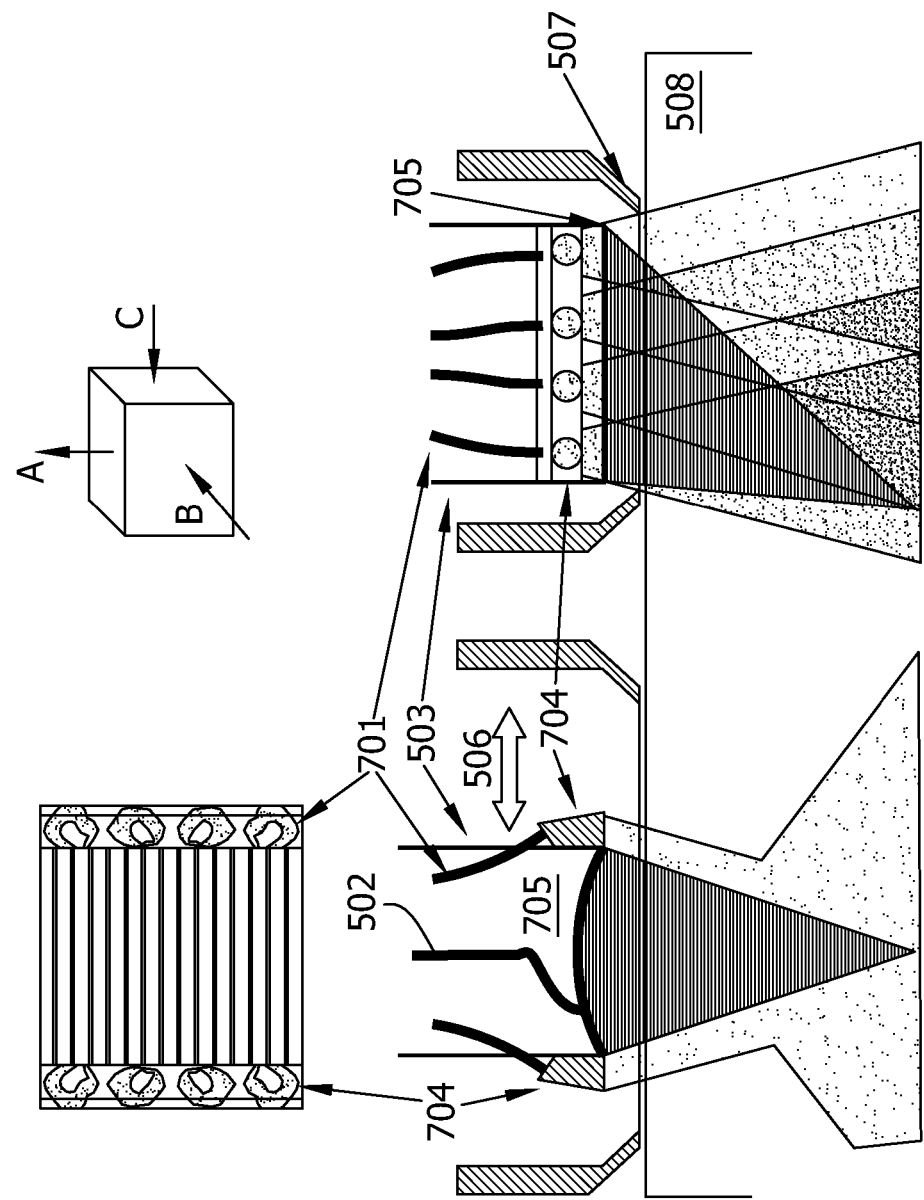
FIG. 7 is a schematic diagram of a third exemplary photoacoustic head that may be used with the measurement system shown in FIG. 3, including a linear phase array of ultrasonic transducers.

FIG. 7 shows a diagram of yet another embodiment of a photoacoustic sensor 700 of the imaging system 100 shown in FIG. 1. The photoacoustic sensor 700 uses a multitude of optical fibers 701, a system of prisms 704 to deliver light pulses, and a one-dimensional cylindrically focused transducer array 705 to form a photoacoustic B-scan image. In this embodiment, the photoacoustic sensor 700 uses translational symmetry instead of cylindrical symmetry. Unlike the embodiments shown in FIGS. 5 and 6, a wedge-shaped light beam is formed instead of a cone-shaped one, and a linear transducer array 705, similar to one used in medical ultrasonic diagnostics, is used to acquire photoacoustic signals. Using beam forming, such a device may produce a complete photoacoustic B-scan image with a single laser pulse, making possible ultrafast real-time photoacoustic imaging with the B-scan frame rate limited by the pulse repetition rate of the laser. Sector scanning the single row of piezoelectric elements produces volumetric photoacoustic images at potential rates of approximately thirty volumetric frames per second.

Figure 8:
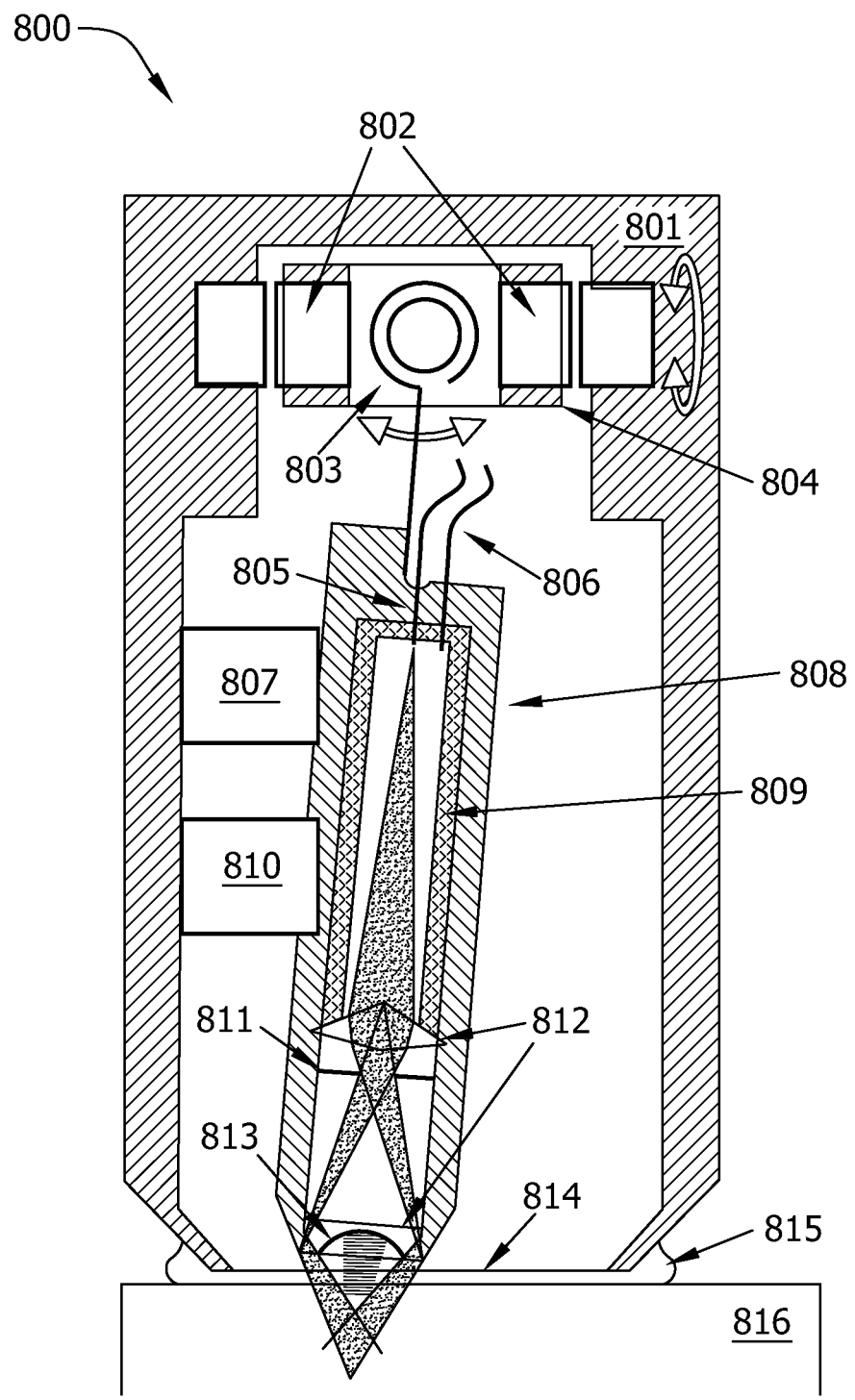
FIG. 8 is a schematic diagram of an exemplary photoacoustic scanner system that uses cantilever beam-based two-dimensional scanning for volumetric imaging.

FIG. 8 is a block diagram of another embodiment of a photoacoustic scanner 800 that uses sector scanning in two perpendicular directions. A laser pulse is coupled into an optical fiber 805, which is coaxially positioned with the focused ultrasonic transducer 813. With the help of the focusing optics 812, the laser light from the fiber 805 is expanded, passed around the transducer, and then converged towards the ultrasonic focus inside the object under investigation 816. The optical focal region overlaps with the focal spot of the ultrasonic transducer 813, thus forming a confocal optical dark-field illumination and ultrasonic detection configuration. The photoacoustic setup is mounted inside a hollow cylindrical cantilever beam 808 supported by a first flexure bearing 803. The bearing 803 is mounted in a frame 804, which is mounted inside a container 801 on second and third flexure bearings 802. The axis of rotation of the second and third bearings 802 is perpendicular to the axis of rotation of the first bearing 803. Tilting of the cantilever beam 808 in two perpendicular directions results in two dimensional scanning along the object surface. The container 801 is filled with immersion liquid and sealed by an optically and acoustically transparent membrane 814. The object (e.g., animal or human) 816 is placed outside the container 801 below the membrane 814, and ultrasonic coupling is further secured by coupling gel 815. The cantilever beam 808 is moved by an actuator 807, and its inclination angle is controlled by a sensor 810. Part of the laser pulse energy is reflected from the focusing optics, such as conical lens 812, and, after multiple reflections from the diffusely reflective coating of an integrating chamber 809, is transmitted by the sensing optical fiber 806 to a photo-detector (not shown). The signal from the photo-detector is used as a reference signal to offset the energy fluctuations of the laser output. An aperture diaphragm 811 screens the photo-detector from ambient light and sample surface reflection.

Figure 9:
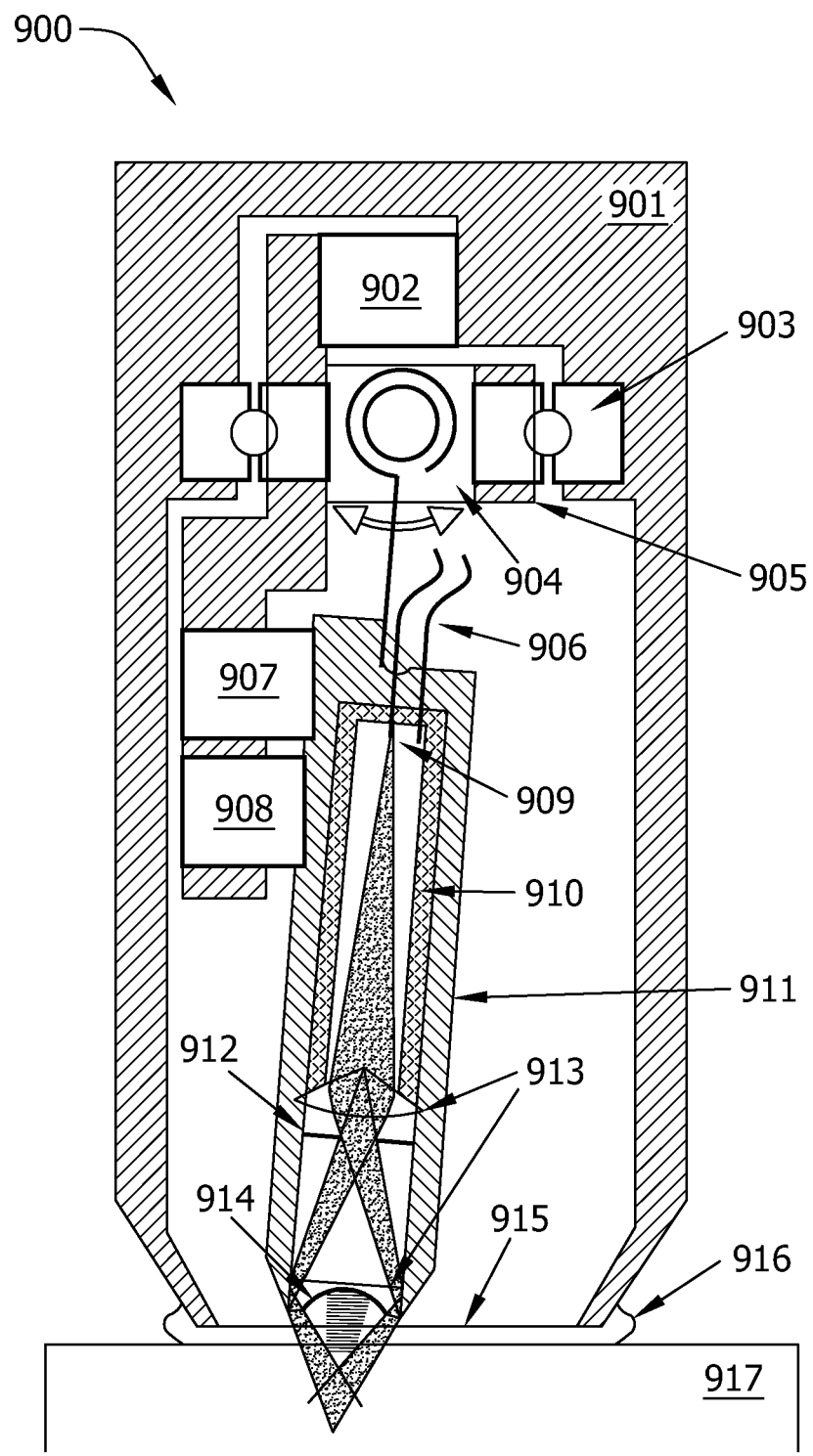
FIG. 9 is a schematic diagram of a second exemplary photoacoustic scanner system that combines cantilever beam scanning and linear translation scanning for volumetric imaging.

FIG. 9 is a block diagram of another embodiment of a photoacoustic scanner 900 that uses sector scanning in one direction and linear scanning in a perpendicular direction. A laser pulse is coupled into optical fiber 909, which is coaxially positioned with a focused ultrasonic transducer 914. With the help of a focusing optics 913, the laser light from the fiber 909 is expanded, passed around the transducer 914, and then converged towards the ultrasonic focus inside the object under investigation 917. The optical focal region overlaps with the focal spot of the ultrasonic transducer 914, thus forming a confocal optical dark-field illumination and ultrasonic detection configuration. The photoacoustic detector setup is mounted inside a hollow cylindrical cantilever beam 911 supported by a flexure bearing 904, which is mounted in a frame 905. The frame 905 is mounted on a translation stage 903 inside a container 901. The axis of rotation of the bearing 904 is perpendicular to the displacement direction of the translation stage 903. Tilting of the cantilever beam 911 in combination with linear motion in a perpendicular direction results in two dimensional scanning along the object surface. The container 901 is filled with immersion liquid and sealed with optically and acoustically transparent membrane 915. The sample (e.g., animal or human) 917 is placed outside the container 901 below the membrane 915, and the ultrasonic coupling is further secured by coupling gel 916. The cantilever beam 911 is moved by an actuator 907, and its inclination angle is controlled by a sensor 908. The translation stage 903 is moved by a motor 902, which may be a combination of a ball screw, belts, a step motor, a voice coil linear actuator, or piezoelectric actuator. Part of the laser pulse energy is reflected from the focusing optics, such as conical lens 913, and, after multiple reflections from the diffusely reflective coating of an integrating chamber 910, is transmitted by the sensing optical fiber 906 to a photo-detector (not shown). The signal from the photo-detector is used as a reference signal to compensate for the energy fluctuations of the laser output. An aperture diaphragm 912 screens the photo-detector from ambient light and sample surface reflections.

Figure 10B:
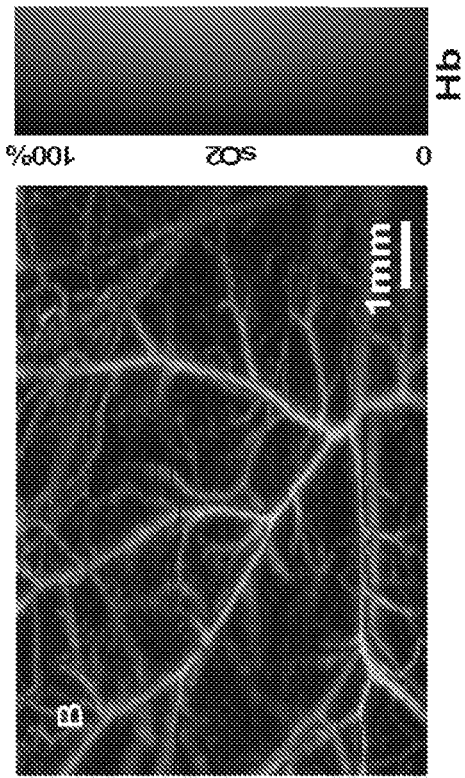
FIG. 10B shows a blood oxygenation level image acquired with photoacoustic imaging.
Figure 10A:
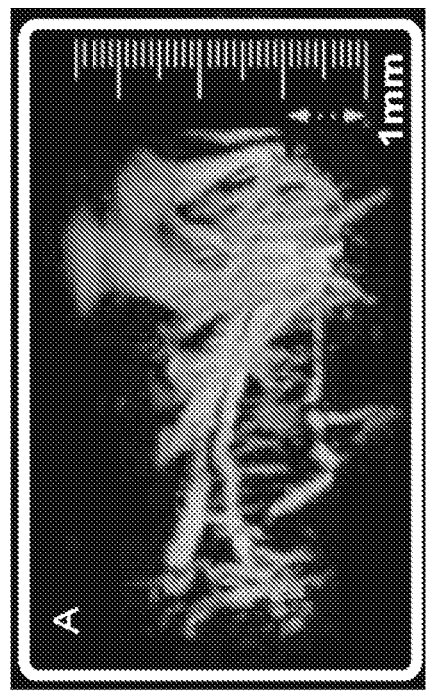
FIG. 10A shows a blood flow image in a mouse prostate taken by an ultrasonic system.

FIG. 10A shows a blood flow image in a mouse prostate taken by an ultrasonic system and FIG. 10B shows a blood oxygenation level image acquired with photoacoustic imaging. More specifically, FIG. 10A shows 3D tumor perfusion and flow architecture in a mouse prostate tumor imaged by an ultrasonic system, and FIG. 10B shows a photoacoustic image of $SO_2$ in subcutaneous blood vessels in a 200-g Sprague-Dawley rat in vivo. Structural image data reflects the total hemoglobin concentration acquired at 584 nm, color reflects the $SO_2$. The combination of these two contrasts can shed light on tissue oxygen consumption within the volume of for example a relatively small tumor or small organ, which reflects the metabolic rate of the tissue.

Figure 11A:
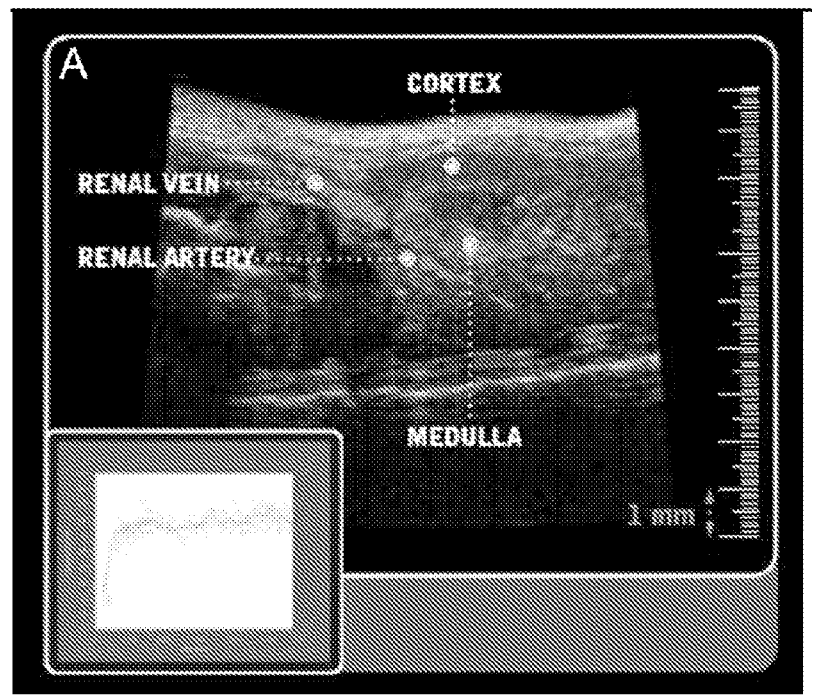
FIG. 11A shows an ultrasonic image of blood vessels.
Figure 11B:
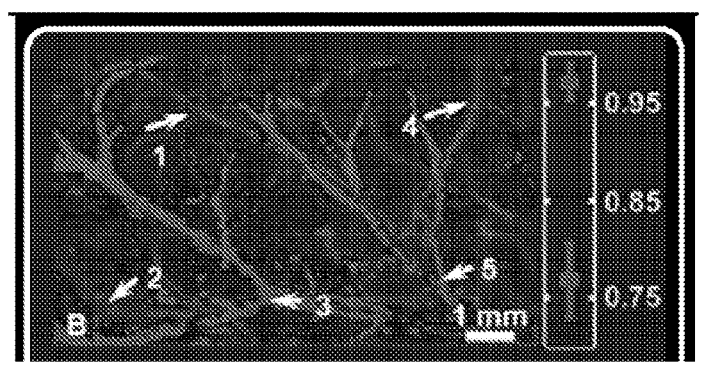
FIG. 11B shows a photoacoustic image of oxygen saturation of hemoglobin ($SO_2$).
Figure 11C:
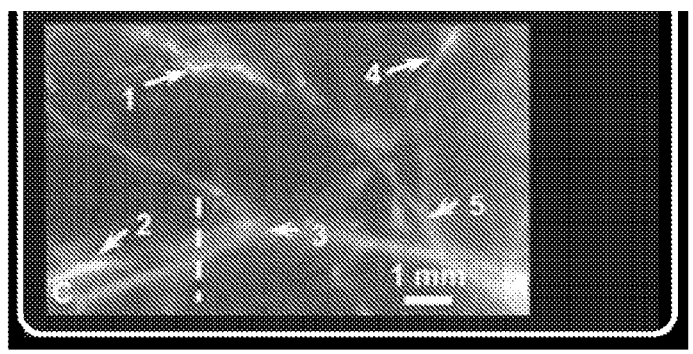
FIG. 11C shows an ex-vivo microsphere-perfusion image of arterioles (red) and venules (blue).

Similarly, a contrast agent enhanced ultrasonic image, as shown in FIG. 11A, taken by an ultrasonic system shows blood perfusion and major veins and arteries but must rely on anatomical cues to distinguish between veins and arteries. By contrast, such a distinction can be made by photoacoustic imaging directly using the imaged oxygen saturation of hemoglobin, as shown in FIG. 11B. This distinction is confirmed as shown in FIG. 11C, which shows ex-vivo microsphere-perfusion image of arterioles (red) and venules (blue).

By recording photoacoustic signals obtained at various optical wavelengths, the optical absorption spectrum of the object may be measured. The optical absorption coefficient is dominated by the absorption of hemoglobin in many cases. Because two forms of hemoglobin—oxygenated and deoxygenated—have distinctly different absorption spectra, one may recover the partial concentrations of the two forms of hemoglobin. This value may be used to quantify the oxygen saturation of hemoglobin and the relative total concentration of hemoglobin. Of course, this example merely illustrates the principle, which may be extended to the measurement of other optical absorbers using two or more excitation optical wavelengths.

Because of the fast frame rate, the device in the embodiments of the invention may combine blood flow measurement into and out of regions of interest using the pulse-Doppler technique with blood oxygenation measurements to estimate oxygen metabolism in tissues and organs. The oxygen metabolic rate ($MRO_2$) is the amount of oxygen consumed in a given tissue region per unit time per 100 g of tissue or of the organ of interest. In typical physiological conditions, since hemoglobin is the dominant carrier of oxygen, the key measure of blood oxygenation is the oxygen saturation of hemoglobin ($SO_2$). Therefore, we have $$MRO_2 \propto (SO_{2,in} - SO_{2,out}) \cdot C_{Hb} \cdot A_{in} \cdot \bar{v}_{in} \qquad \text{Eq. (1)}$$

Here, $A_{in}$, is the area of the incoming vessel, $\bar{v}_{in}$ is the mean flow velocity of blood in the incoming vessel, and $C_{Hb}$ is the total concentration of hemoglobin. While $A_{in}$, and $\bar{v}_{in}$, may be estimated using ultrasound imaging, $SO_2$, and relative $C_{Hb}$, may be estimated from multi-wavelength photoacoustic methods.

FIG. 12 is a flowchart 1200 illustrating an exemplary photoacoustic tomography imaging method that characterizes a tissue by focusing 1201 one or more laser pulses on a region of interest in the tissue and illuminating the region of interest. More specifically, the laser pulses are emitted from collimating optics mounted on a cantilever beam that is flexibly mounted within a handheld device. In one embodiment, the cantilever beam is a semi-rigid cantilever beam supported by a flexure bearing. In another embodiment, the cantilever beam is a fixed-end flexible cantilever beam. In another embodiment, the cantilever beam is mounted with two degrees of freedom and is supported by perpendicular flexure bearings. In yet another embodiment, the cantilever beam is supported by a flexure bearing that is coupled to a linear scanning cage. Acoustic waves induced in the object by optical absorption are received 1202 and a signal is generated 1203 representative of the acoustic waves using one or more ultrasonic transducers that are focused on the same region of interest. The signal is then used to image 1204 the structure or composition of the object. The one or more laser pulses are focused by an optical assembly, typically including lenses, prisms, and/or mirrors, which converges the laser light towards the focal point of the ultrasonic transducer. The focused laser light selectively heats the region of interest, causing the object to expand and produce a pressure wave having a temporal profile that reflects the optical absorption and thermo-mechanical properties of the object. In addition to a single-element, focused ultrasonic transducer, an annular array of ultrasonic transducers may be used to enhance the depth of field of the imaging system by using synthetic aperture image reconstruction. The assembly of the ultrasonic transducer and laser pulse focusing optics are positioned on a cantilever beam and scanned together, performing fast one-directional or two-directional sector scanning of the object. The cantilever beam is suspended inside a closed, liquid-filled container, which has an acoustically and optically transparent window on a side of the transducer-light delivery optics assembly. The window is positioned on an object surface and acoustic coupling gel is applied. The received acoustic waves are digitized and the digitized acoustic waves are transmitted to a computer for analysis. An image of the object is then formed from the digitized acoustic waves.

FIG. 13 is a flowchart 1300 illustrating an exemplary method for determining an oxygen metabolic rate ($MRO_2$) within a biological tissue using a handheld device. A plurality of multi-wavelength light pulses are focused 1302 on a region of interest in the tissue and illuminating the region of interest. More specifically, the laser pulses are emitted from collimating optics mounted on a cantilever beam that is flexibly mounted within a handheld device. In one embodiment, the cantilever beam is a semi-rigid cantilever beam supported by a flexure bearing. In another embodiment, the cantilever beam is a fixed-end flexible cantilever beam. In another embodiment, the cantilever beam is mounted with two degrees of freedom and is supported by perpendicular flexure bearings. In yet another embodiment, the cantilever beam is supported by a flexure bearing that is coupled to a linear scanning cage. Acoustic waves induced in the object by optical absorption are received 1304 using one or more ultrasonic transducers that are focused on the same region of interest. The signal is then used to detect 1306 an area of an incoming vessel within the predetermined area, a mean flow velocity of blood in the incoming vessel, and a total concentration of hemoglobin. The area of the incoming vessel and the mean flow velocity are based on measurements obtained by ultrasound imaging, and the total concentration of hemoglobin is based on measurements obtained by the plurality of multi-wavelength light pulses. The $MRO_2$ is determined 1308 based on the area of the incoming vessel, the mean flow velocity of blood in the incoming vessel, and the total concentration of hemoglobin using Equation (1) as explained above. The $MRO_2$ is the amount of oxygen consumed in a given tissue region per unit time per 100 g of tissue or of the organ of interest. In typical physiological conditions, since hemoglobin is the dominant carrier of oxygen, the key measure of blood oxygenation is the oxygen saturation of hemoglobin ($SO_2$). The one or more laser pulses are focused by an optical assembly, typically including lenses, prisms, and/or mirrors, which converges the laser light towards the focal point of the ultrasonic transducer. The focused laser light selectively heats the region of interest, causing the object to expand and produce a pressure wave having a temporal profile that reflects the optical absorption and thermo-mechanical properties of the object. In addition to a single-element, focused ultrasonic transducer, an annular array of ultrasonic transducers may be used to enhance the depth of field of the imaging system by using synthetic aperture image reconstruction. The assembly of the ultrasonic transducer and laser pulse focusing optics are positioned on a cantilever beam and scanned together, performing fast one-directional or two-directional sector scanning of the object. The cantilever beam is suspended inside a closed, liquid-filled container, which has an acoustically and optically transparent window on a side of the transducer-light delivery optics assembly. The window is positioned on an object surface and acoustic coupling gel is applied. The received acoustic waves are digitized and the digitized acoustic waves are transmitted to a computer for analysis. An image of the object is then formed from the digitized acoustic waves.

By implementing photoacoustic imaging capabilities on a commercial ultrasound system, ultrasound and photoacoustic pulse sequences may be interleaved to obtain (1) structural images from ultrasound B-mode scans, (2) functional images of total hemoglobin concentration from photoacoustic scans, (3) functional images of hemoglobin oxygen saturation ($SO_2$) from photoacoustic scans, and (4) images of melanin concentration from photoacoustic scans as well. Therefore, photoacoustic imaging will significantly enrich the contrast of ultrasound imaging and provide a wealth of functional information.

It will be understood that the particular embodiments described herein are shown by way of illustration and not as limitations of the invention. The principal features of this invention may be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All of the compositions and/or methods disclosed and claimed herein may be made and executed without undue experimentation in light of the present disclosure. While the compositions and methods of this invention have been described in terms of embodiments, it will be apparent to those of skill in the art that variations may be applied to the compositions and/or methods and in the operations or in the sequence of operations of the method described herein without departing from the concept, spirit and scope of the invention. All such similar substitutes and modifications apparent to those skilled in the art are deemed to be within the spirit, scope and concept of the invention as defined by the appended claims.

It will be understood by those of skill in the art that information and signals may be represented using any of a variety of different technologies and techniques (e.g., data, instructions, commands, information, signals, bits, symbols, and chips may be represented by voltages, currents, electromagnetic waves, magnetic fields or particles, optical fields or particles, or any combination thereof). Likewise, the various illustrative logical blocks, modules, circuits, and algorithm operations described herein may be implemented as electronic hardware, computer software, or combinations of both, depending on the application and functionality. Moreover, the various logical blocks, modules, and circuits described herein may be implemented or performed with a general purpose processor (e.g., microprocessor, conventional processor, controller, microcontroller, state machine or combination of computing devices), a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. Similarly, operations of a method or process described herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. Although embodiments of the invention have been described in detail, it will be understood by those skilled in the art that various modifications may be made therein without departing from the spirit and scope of the invention as set forth in the appended claims.

What is claimed is:

1. A method for noninvasively imaging biological tissue using a handheld device, said method comprising:
   focusing at least one light pulse suitable for photoacoustic imaging from an optical fiber into a predetermined area inside the tissue, wherein the optical fiber is positioned on a cantilever beam that is mounted at one extreme end using at least one flexure bearing;
   detecting acoustic waves emitted from the predetermined area in response to the at least one light pulse using a transducer positioned on the cantilever beam; and
   generating an image of the predetermined area based on a signal generated by the transducer representative of the acoustic waves;
   wherein the optical fiber and the transducer positioned on the cantilever beam are configured to be sector scanned together.

2. A method in accordance with claim 1, wherein focusing at least one light pulse comprises focusing the at least one light pulse using at least one optical assembly.

3. A method in accordance with claim 1, further comprising inducing the acoustic waves in the predetermined area via optical absorption by the predetermined area of the at least one light pulse, wherein the predetermined area is heated using the at least one light pulse.

4. A method in accordance with claim 1, wherein detecting the acoustic waves comprises detecting the acoustic waves using a transducer array having a plurality of elements focused on the predetermined area.

5. A method in accordance with claim 1, further comprising digitizing the signal generated by the transducer, wherein the image is generated using the digitized signal.

6. A method in accordance with claim 1, further comprising sector scanning the cantilever beam by driving the cantilever beam and measuring a current location of the transducer using a motor controller, said focusing at least one light pulse comprises emitting the at least one light pulse at a predefined transducer location.

7. A method in accordance with claim 1, wherein the handheld device comprises:
   a laser;
   an optical assembly configured to focus at least one light pulse emitted by said laser into the predetermined area inside the object; and
   the transducer, wherein said optical assembly and said transducer are positioned on the cantilever beam, the cantilever beam being flexibly mounted within a closed, liquid-filled container to facilitate one of one-dimensional scanning of the predetermined area inside the object and two-dimensional scanning of the predetermined area inside the object.

8. A method in accordance with claim 7, wherein said at least one flexure bearing is coupled to a linear stage.

9. A method in accordance with claim 7, wherein said cantilever beam comprises a fixed-end, flexible cantilever beam.

10. A method in accordance with claim 7, wherein said transducer comprises a single-element focused ultrasonic transducer.

11. A method in accordance with claim 7, wherein said transducer comprises an array of ultrasonic transducers.

12. A method in accordance with claim 7, wherein said container comprises an acoustically and optically transparent window positioned with respect to said optical assembly.

13. A method in accordance with claim 7, wherein said transducer transmits the signal to a digitizer for use in generating the image.

14. A method in accordance with claim 13, wherein said laser is configured to emit the at least one light pulse at a predefined transducer location based on a measurement of a current location of said transducer by a motor controller.

15. A method in accordance with claim 1, further comprising mounting the cantilever beam within a container.

16. A method in accordance with claim 15, further comprising filling the container with an immersion liquid such that the cantilever beam is suspended in the immersion liquid.

17. A method in accordance with claim 15, further comprising securing the container to the biological tissue using a coupling gel.

18. A method in accordance with claim 15, further comprising sealing the container with an optically and acoustically transparent membrane.

19. A method in accordance with claim 1, wherein the optical fiber and the transducer are coaxial with one another.

20. A method in accordance with claim 1, further comprising controlling an inclination angle of the cantilever beam using a sensor.

* * * * *